(12) United States Patent
Tomita (10) Patent No.: US 12,171,975 B1
(45) Date of Patent: Dec. 24, 2024

(54) STERILE CONNECTOR

(71) Applicant: ABLE Corporation, Tokyo (JP)

(72) Inventor: Satoshi Tomita, Tokyo (JP)

(73) Assignee: ABLE CORPORATION, Tokyo (JP)

( * ) Notice: Subject to any disclaimer, the term of this patent is extended or adjusted under 35 U.S.C. 154(b) by 0 days.

(21) Appl. No.: 18/810,871

(22) Filed: Aug. 21, 2024

(30) Foreign Application Priority Data

Oct. 18, 2023 (JP) ................................. 2023-179553

(51) Int. Cl.
*F16L 37/098* (2006.01)
*A61M 39/18* (2006.01)
*F16L 37/02* (2006.01)
*A61M 39/10* (2006.01)

(52) U.S. Cl.
CPC ............. *A61M 39/18* (2013.01); *F16L 37/02* (2013.01); *A61M 2039/1027* (2013.01)

(58) Field of Classification Search
CPC ......... F16L 37/02; F16L 37/025; F16L 37/04; F16L 37/084; F16L 37/0847; F16L 37/096; F16L 37/098; F16L 37/12; F16L 37/133; F16L 2201/40; F16L 2201/44
See application file for complete search history.

(56) References Cited

U.S. PATENT DOCUMENTS

| | | | | |
|---|---|---|---|---|
| 4,418,945 A * | 12/1983 | Kellogg | ................ | A61M 39/14 285/70 |
| 10,247,342 B2 * | 4/2019 | Kesselaar | ............. | A61M 39/18 |
| 11,141,578 B2 * | 10/2021 | Shevitz | ................... | F16L 23/02 |
| 11,796,109 B2 * | 10/2023 | Durrant | ................. | A61M 39/12 |
| 2003/0030272 A1 * | 2/2003 | Johnson | ................... | F16L 29/00 285/70 |
| 2010/0230961 A1 * | 9/2010 | Johnson | ............. | F16L 37/0985 285/352 |

(Continued)

FOREIGN PATENT DOCUMENTS

| JP | 2017-518749 A | 7/2017 |
|---|---|---|
| JP | 2021-037035 A | 11/2021 |
| WO | WO 2015/184189 A1 | 12/2015 |

OTHER PUBLICATIONS

Notice of Reasons for Refusal for JP Patent Application No. 2023-179553 dated Feb. 6, 2024, 4 pages.

(Continued)

*Primary Examiner* — Aaron M Dunwoody
(74) *Attorney, Agent, or Firm* — FROST BROWN TODD LLP (57) ABSTRACT

A sterile connector including: first and second connectors of the same shape including: a first (second) body portion including a first (second) joining surface; a first engaging member; and a first (second) fitting portion that fits with the first (second) tube, which is provided on a back surface of the first (second) joining surface of the first (second) body portion and which has a tip end portion for tightening the first (second) tube, an end face of the first (second) tube is configured to be positioned to project beyond the first (second) joining surface, and the sterile connector is configured such that when the first connector and the second connector are engaged such that the first joining surface faces the second joining surface, the end face of the first tube and the end face of the second tube are compressed with each other.

8 Claims, 4 Drawing Sheets

(56) References Cited

U.S. PATENT DOCUMENTS

| | | | | |
|---|---|---|---|---|
| 2013/0289517 A1* | 10/2013 | Williams | .............. | F16L 37/098 |
| | | | | 604/500 |
| 2015/0061282 A1* | 3/2015 | Faldt | .................... | A61M 39/16 |
| | | | | 285/124.5 |
| 2016/0186906 A1* | 6/2016 | Blake | ................. | A61M 39/1011 |
| | | | | 285/319 |
| 2017/0284584 A1* | 10/2017 | Kesselaar | .......... | A61M 39/1011 |
| 2018/0264251 A1* | 9/2018 | Lofving | ................ | A61M 39/18 |
| 2019/0167971 A1* | 6/2019 | Shevitz | ................. | A61M 39/10 |
| 2021/0062946 A1* | 3/2021 | Gerst | .................... | F16L 55/105 |
| 2021/0403851 A1* | 12/2021 | Casura | ................... | C12M 23/40 |
| 2022/0252194 A1* | 8/2022 | Benson | .................. | F16L 37/30 |
| 2022/0381384 A1* | 12/2022 | Coscia | .................. | F16L 37/30 |
| 2023/0121701 A1* | 4/2023 | Casura | ................. | F16L 37/098 |
| | | | | 285/305 |

OTHER PUBLICATIONS

Decision to Grant a Patent for JP Patent Application No. 2023-179553 dated Mar. 22, 2024, 2 pages.

* cited by examiner

STERILE CONNECTOR

TECHNICAL FIELD

The present invention relates to a sterile connector for connecting tubes (pipes for communicating fluid) with one another.

BACKGROUND ART

Biopharmaceuticals are manufactured through various steps, such as culturing cells and microorganisms, purifying culture solution, inactivating cells and other substances, concentrating culture solution, and storing manufactured bulk drug. Each step requires the use of a container that is optimized for the step, which necessitates transfer of liquid between the containers. In the field of biopharmaceuticals, manufacturing processes must be carried out in a sterile manner, and the transfer of liquid between containers must also be carried out in a sterile manner. In order to meet this requirement, techniques have been developed to connect two containers in a general environment in a sterile manner, and various types of sterile connectors have been proposed.

PRIOR ART PUBLICATION

Patent Document

[Patent Document 1] Japanese Patent Application Publication 2021-37035

SUMMARY OF THE INVENTION

Problem to be Solved by the Invention

Although the sterile connector of Patent Document 1 is intended to improve manufacturing efficiency by reducing the number of components (paragraphs 0007, 0008), there are multiple components (body part 3, elastic membrane 5, elastic member 21, distribution hole member 20) interposed between the tubes (pipes for communicating fluid) to be connected, and therefore, there is a demand for the development of simpler sterile connectors.

In view of the above, the purpose of the present invention is to provide a sterile connector for connecting tubes, which has a simpler configuration and can achieve a high level of sterility.

Means for Solving the Problem (Configuration 1)
A sterile connector including a first connector to be attached to a first tube, and a second connector to be attached to a second tube,
in which the first connector includes:
a first body portion including a first joining surface;
a first engaging member for engaging with the second connector; and
a first fitting portion that fits with the first tube, which is provided on a back surface of the first joining surface of the first body portion and which has a tip end portion for tightening the first tube, and
in which the second connector includes:
a second body portion including a second joining surface;
a second engaging member for engaging with the first connector; and
a second fitting portion that fits with the second tube, which is provided on a back surface of the second joining surface of the second body portion and which has a tip end portion for tightening the second tube,
in which the first connector and the second connector have the same shape,
in which the first connector is attached to the first tube such that an end face of the first tube is positioned to project beyond the first joining surface, or the second connector is attached to the second tube such that an end face of the second tube is positioned to project beyond the second joining surface, and
in which the sterile connector is configured such that, when the first connector and the second connector are engaged such that the first joining surface faces the second joining surface, the end face of the first tube and the end face of the second tube are compressed with each other.
(Configuration 2)
The sterile connector according to Configuration 1, in which the first fitting portion includes a first spacing where the first tube is not tightened, and in which the second fitting portion includes a second spacing where the second tube is not tightened.
(Configuration 3)
The sterile connector according to Configuration 2, in which the first tube includes a first thick diameter portion where an outer diameter increases toward the first body portion in the first spacing, and in which the second tube includes a second thick diameter portion where an outer diameter increases toward the second body portion in the second spacing.
(Configuration 4)
The sterile connector according to any one of Configurations 1 to 3, in which the end face of the first tube has a convex curve in cross-section along a longitudinal direction of the first tube, or in which the end face of the second tube has a convex curve in cross-section along a longitudinal direction of the second tube.
(Configuration 5)
The sterile connector according to any one of Configurations 1 to 4, in which a tip end portion of the first tube and the tip end portion of the second tube are configured as a flange.
(Configuration 6)
The sterile connector according to any one of Configurations 1 to 5, configured such that inner diameters of the first tube and the second tube do not change.
(Configuration 7)
The sterile connector according to any one of Configurations 1 to 6, in which the first connector includes a first protective sheet that covers the first joining surface and the end face of the first tube, in which the second connector includes a second protective sheet that covers the second joining surface and the end face of the second tube, in which the first body portion and the second body portion are configured from polypropylene, in which the first protective sheet and the second protective sheet are configured from polyethylene, and in which the first protective sheet and the second protective sheet are fixed to the first body portion and the second body portion by thermal welding and are removed after the first connector and the second connector are engaged.
(Configuration 8)
The sterile connector according to any one of Configurations 1 to 6, in which the first connector includes a first protective sheet that covers the first joining surface and the end face of the first tube, in which the second connector includes a second protective sheet that covers the second joining surface and the end face of the second tube, in which the first body portion and the second body portion are configured from polycarbonate, in which the first protective sheet and the second protective sheet are configured from polyethylene, and in which the first protective sheet and the second protective sheet are fixed to the first body portion and the second body portion via an adhesive and are removed after the first connector and the second connector are engaged.

Effect of the Invention

The sterile connector of the present invention can provide a connector that can achieve a high level of sterility with a simpler configuration.

EMBODIMENTS FOR CARRYING OUT THE INVENTION

The embodiment of the present invention is specifically explained referring to the drawings. The embodiment given below is one of the embodiments in embodying the present invention, and by no means limits the present invention within such a scope.

Figure 1:
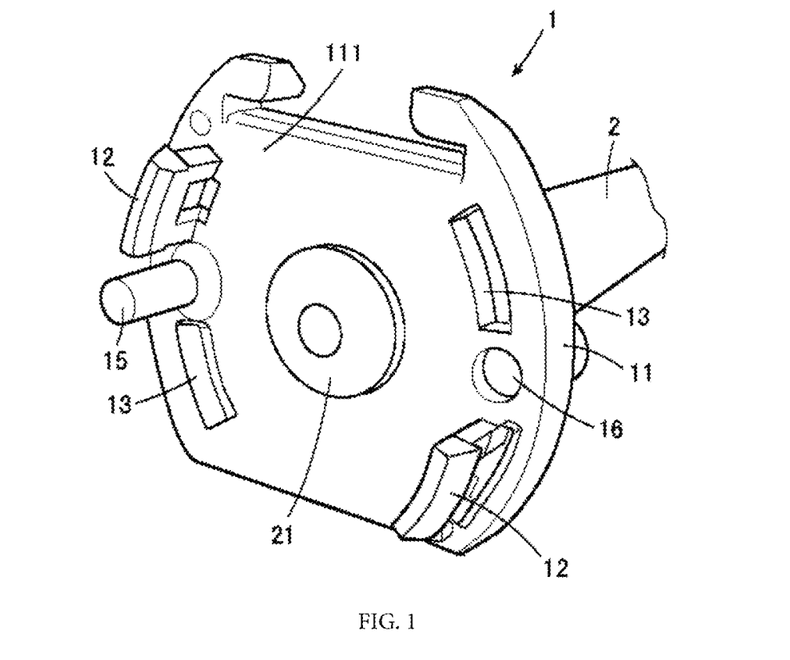
FIG. 1 is a perspective view showing a sterile connector (one of a pair of connectors of the same shape) of an embodiment according the present invention.
Figure 2:
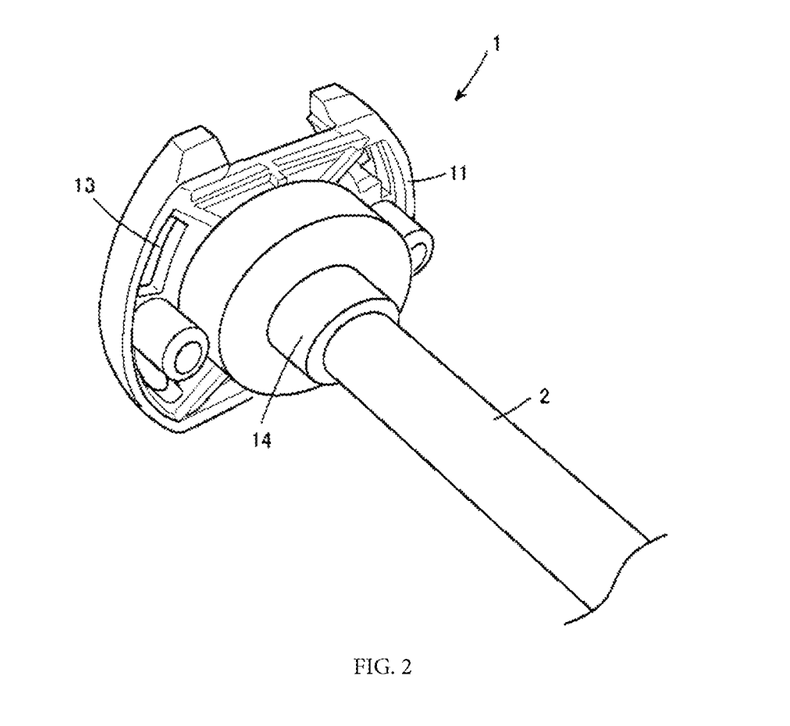
FIG. 2 is another perspective view showing the sterile connector of the embodiment.
Figure 3:
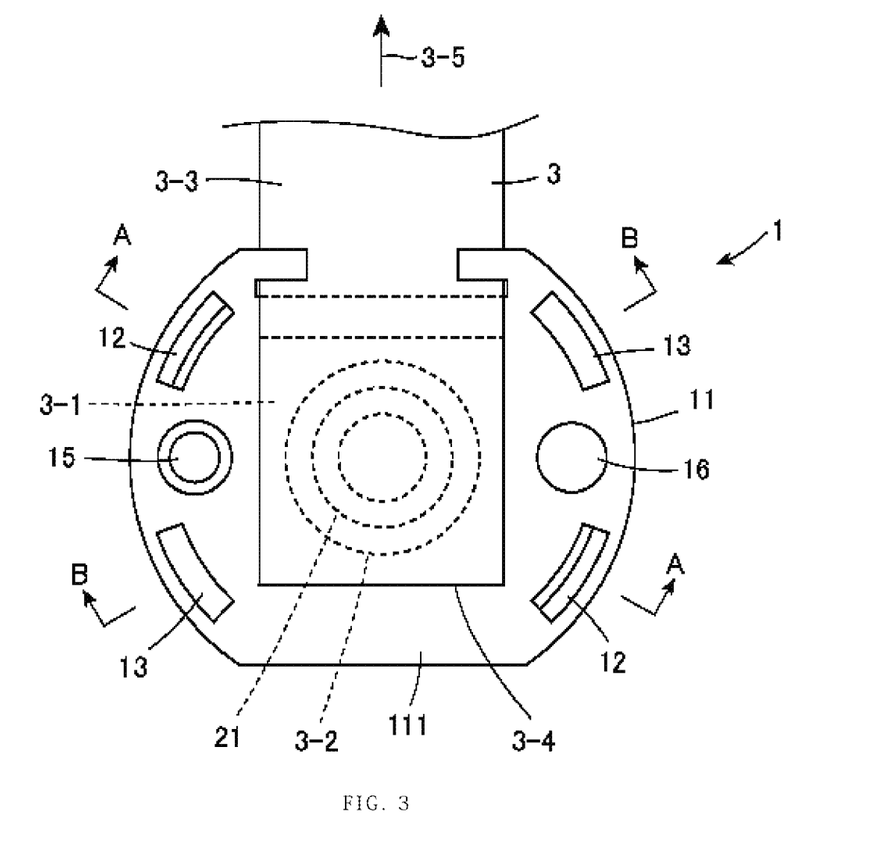
FIG. 3 is a front view showing the sterile connector of the embodiment.
Figure 4A:
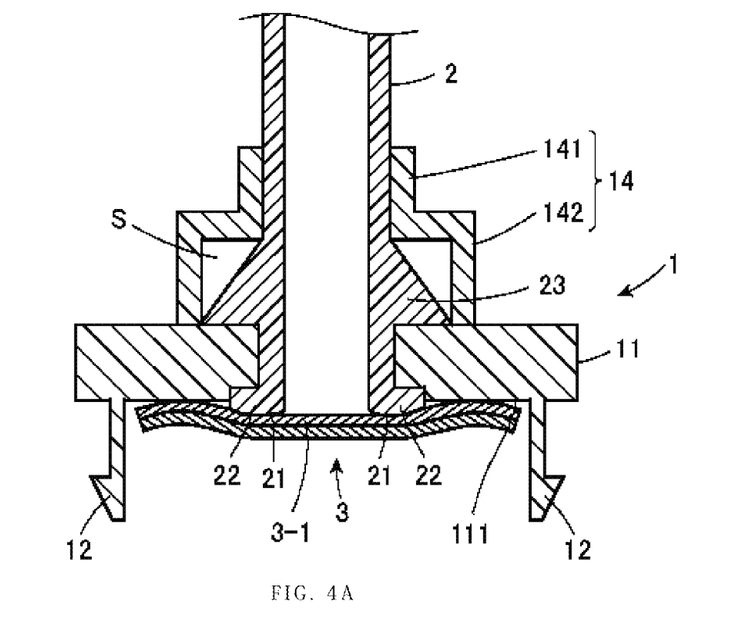
FIG. 4A is a cross-sectional view of the sterile connector of the embodiment, taken along line A-A of FIG. 3.
Figure 4B:
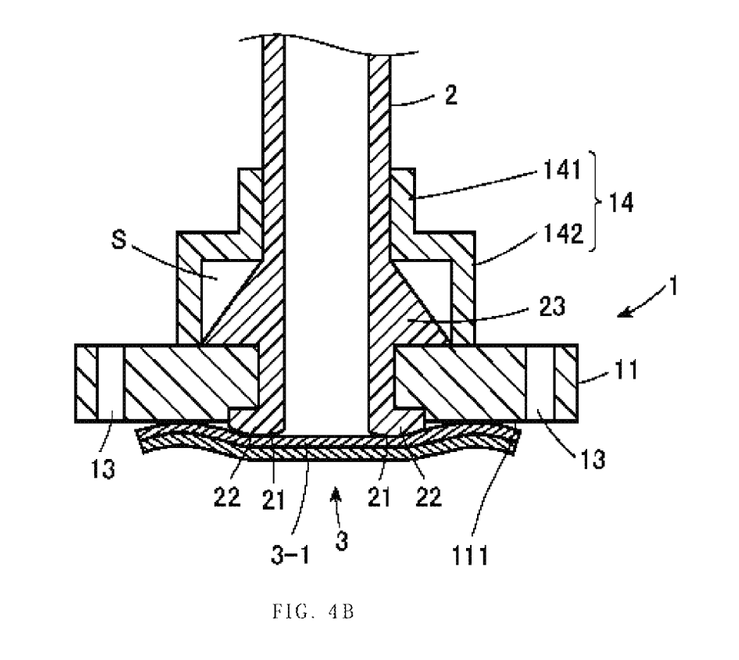
FIG. 4B is a cross-sectional view of the sterile connector of the embodiment, taken along line B-B of FIG. 3.

FIG. 1 is a perspective view showing a sterile connector (first connector which is one of a pair of connectors of the same shape) of an embodiment according the present invention viewed from the joining surface side, and FIG. 2 is a perspective view seen from a back surface. FIG. 3 is a front view of the sterile connector (one of a pair of connectors of the same shape) of this embodiment, and FIGS. 4A-4B are cross-sectional views (FIG. 4A: cross-sectional view along line A-A in FIG. 3, FIG. 4B: cross-sectional view along line B-B in FIG. 3).

The sterile connector of this embodiment is used to connect two tubes with one another, which are tubes for communicating fluid, and is configured to prevent the entry of microorganisms and other substances from the joint.

In other words, the first tube and the second tube are joined in a sterile manner by engaging the first connector attached to an end portion of one tube (first tube) and the second connector attached to an end portion of the other tube (second tube).

In this embodiment, the first connector (including a first protective sheet) and the second connector (including a second protective sheet) of the sterile connector, and the first tube and the second tube have the same shape (same in female and male shapes). The configurations of one connector (first connector 1) and one tube (first tube 2) are explained below.

As shown in FIGS. 1 and 2, the first connector 1 includes:
a first body portion 11 having a first joining surface 111;
an engaging projection 12 which is a first engaging member for engaging with a second connector (having the same configuration as the first connector 1);
an engaging hole 13 that engages with a second engaging member (same type as the engaging projection 12) of the second connector;
a first fitting portion 14 fitting with the first tube 2, which is provided on a back surface of the first joining surface 111 of the first body portion 11 and which has a tip end portion 141 for tightening the first tube 2;
a boss 15 for alignment; and
a boss hole 16 for receiving the boss of the second connector.

As shown in FIGS. 3 to 5A-5B, the first connector includes a first protective sheet 3 covering an end face 21 of the first tube 2. The first protective sheet 3 is removed after the first connector and the second connector are engaged with one another. FIGS. 4A-5B are rather exaggerated schematic views for easier view (e.g., the first protective sheet 3 is shown thicker).

The first body portion 11 is a substantially disk-like plate member, and the first joining surface 111 is formed flat excluding the members for engagement (e.g., engaging projection 12, boss 15).

In the center of the first body portion 11, a hole is formed through which the first tube 2 is inserted, and on the first joining surface 111 side of the hole, a counterbore (recess) is formed to receive a flange portion 22 of the first tube 2.

The first body portion 11 of this embodiment is configured from polypropylene.

Although the first body portion having a substantially disk-shaped outer circumferential shape is given herein as an example, the contour of the first body portion can have any outer circumferential shape.

The first fitting portion 14 is joined to the back surface side of the first body portion 11 (opposite the first joining surface 111).

The first fitting portion 14 functions as a retainer that fits and retains the first tube 2, and in this embodiment, has a configuration in which two cylindrical members with different diameters are joined together as shown in FIGS. 2, 4A-4B, etc.

The tip end portion 141 has an inner diameter that is slightly smaller than the outer diameter of the first tube 2, and is configured to tighten the first tube 2 (at least to contact the outer periphery of the first tube 2) with the tip end portion 141 attached to the first tube 2. The "tip end" of the tip end portion 141 is the "proximal end" when the end portion of the first tube 2 (the end portion to which the first connector 1 is attached) is viewed as the tip end side.

On the other hand, a large diameter portion 142 is formed so that its inner diameter is larger than the outer diameter of the first tube 2 (first thick diameter portion 23) (equivalent at the maximum diameter portion of the first thick diameter portion 23) and forms a first spacing S therein. As a variation, the large diameter portion can be formed so that its inner diameter is the same as the contour of the first thick diameter portion or smaller than the first thick diameter portion (so that the inner surface of the large diameter portion contacts the first thick diameter portion 23).

The first tube 2 is a resilient, elastic, and flexible tube, such as a fluorine resin tube or silicone tube, for example, and can be selected according to the object.

As shown in FIGS. 4A-4B, the first tube 2 has the first thick diameter portion 23 whose outer diameter increases toward the first body portion 11 in the first spacing S within the large diameter portion 142.

As shown in FIGS. 4A-4B, the first tube 2 has the flange portion 22 where the tip end portion of the first tube 2 is configured to be thick (flanged), and the end face 21 of the first tube 2 has a projecting ("projecting down" in FIGS. 4A-4B) curve.

The first connector 1 and the first tube 2 are configured so that when the first connector 1 is attached to the first tube 2, the end face 21 of the first tube projects beyond the first joining surface 111, as shown in FIGS. 4A-4B. Thus, it is configured such that when the first connector 1 and the second connector are engaged so that the first joining surface 111 faces the second joining surface (joining surface of the second connector having the same structure as the first connector 1), the end face 21 of the first tube 2 and the end face of the second tube (end face of the second tube having the same structure as the first tube 2) are compressed with each other.

As shown in FIGS. 4A-4B, it is configured such that the inner diameter of the first tube 2 does not substantially change when the first connector 1 is attached to the first tube 2.

The first protective sheet 3 is fixed to the first joining surface 111 of the first body portion 11 so as to cover the end face 21 of the first tube 2. The first protective sheet 3 seals the inside of the first tube 2 and the tip end portion (end face 21) in a sterile manner, thereby maintaining the inside of the sterile connector 1 sterile even under general environment.

The first protective sheet 3 of this embodiment is configured from polyethylene. Specifically, Tyvek® can be utilized for the first protective sheet 3.

The first protective sheet 3 is configured to extend outward from the first body portion 11 to be removed after engaging the connector (see FIG. 3), and is fixed to the first body portion 11 by thermal welding. The first protective sheet 3 is configured for removal by pulling the portion projecting outward after the connector is joined.

In detail, the first protective sheet 3 has a sealing portion 3-1 that seals the first tube in a sterile manner, a pulling portion 3-3 to be pulled by a user and removed after joining the connector, and a folded portion 3-4 to be folded back between the sealing portion 3-1 and the pulling portion 3-3. This configuration makes it possible to remove the protective sheet by pulling the pulling portion 3-3 in the direction of arrow 3-5 even when the sterile connectors are joined and the protective sheet is strongly pinched between the end faces of the tubes (see FIG. 5B), enabling sterile and liquid-tight connection of the sterile connectors.

While the sealing portion 3-1 is fixed to the first joining surface 111 of the first body portion 11 so as to cover the end face of the first tube 2, the method of fixing can be selected optimally in accordance with applications and materials. For example, if the first connector 1 is configured from polypropylene, they can be fixed by thermal welding. Alternatively, if the first connector 1 is configured from polycarbonate, they can be fixed via an adhesive. In either case, the first protective sheet 3 is fixed to the first joining surface 111 so that a fixing region 3-2, which is to be fixed to the first joining surface 111, surrounds the end face 21 of the first tube 2. Thus, by fixing the first protective sheet 3 and the first joining surface 111 in a region outside the end face 21, it is possible to maintain the inside of the connector sterile.

An overview of attaching the first connector 1 to the first tube 2 has the following steps.

Step of fitting the first body portion 11 to the first tube 2;
Step of inserting the first tube 2 into the first fitting portion 14;
Step of joining (adhering, thermal welding, etc.) the first fitting portion 14 to the first body portion 11; and
Step of fixing the first protective sheet 3 to the first joining surface 111 of the first body portion 11.

Each of the above steps results in the attached state of the first connector 1 as shown in FIGS. 1 to 4A-4B (the first protective sheet 3 is not shown in FIGS. 1 and 2). As can be understood from the above, the attached state of the first connector 1 can be achieved by a relatively easy and simple process.

The sterile connector manufactured as described above is used with the tip end portion of the first tube 2 (tip end opposite from the end face 21) connected to various containers. Examples of containers to which the sterile connector is connected include, but are not limited to, containers for culture, medium transport (supply), purification/concentration, and storage. Sterilizing (e.g., γ sterilization, electron beam sterilization) the container and the sterile connector while connected to these containers enables the container and the sterile connector to be sterilized to the level required for their intended use (e.g., for manufacturing biopharmaceuticals). In particular, since the end face 21 of the first tube 2 of the sterile connector is sealed by the first protective sheet 3, the inside of the sterile connector remains sterile even when placed in a general environment after the sterilization process. Since the sterile connectors are configured to allow sterile connection to one another in a general environment, it is possible to transfer fluids from one container to another in a sterile manner. As an example, an application such as supplying culture medium to a culture container in the general environment can be assumed by engaging (sterilely connecting) a sterile connector connected to a culture container and a sterile connector connected to a medium supply container.

The second tube, which is the other tube to be connected, is also fitted with the second connector. As mentioned above, the second tube and the second connector have the same configuration as the first tube 2 and the first connector 1 (the first tube and the first connector are distinguished from the second tube and the second connector hereinafter by adding "second" to each configuration (reference numerals are identical)). The first tube and the second tube are respectively connected to different containers (containers in which fluid is planned to be transferred therebetween). The procedure for connecting the paired sterile connectors is described below.

The first connector 1 and the second connector 1 attached to each tube are placed to face each other so that respective first joining surface 111 and second joining surface 111 face each other (see FIG. 5A), and the first engaging projection 12 and the second engaging hole 13, and the second engaging projection 12 and the first engaging hole 13 are engaged respectively. Thus, the first connector 1 and the second connector 1 (sterile connectors with respect to each other) are fixed.

The first protective sheet 3 and the second protective sheet 3 are then removed simultaneously by pulling the projecting portions (pulling portions 3-3) of the first protective sheet 3 and the second protective sheet 3 together.

Figure 5A:
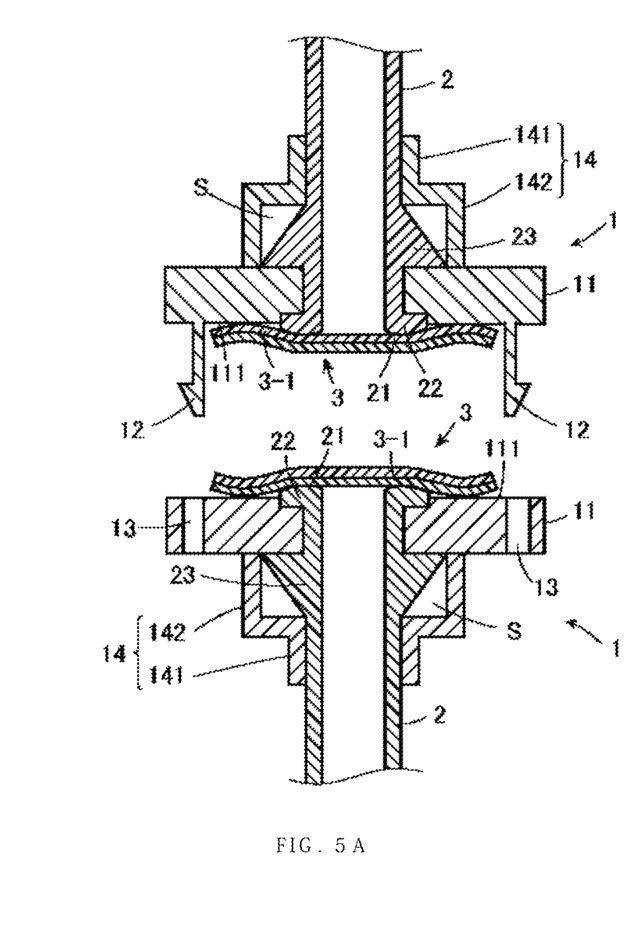
FIG. 5A is a cross-sectional view showing a disconnected state of the sterile connector of the embodiment.
Figure 5B:
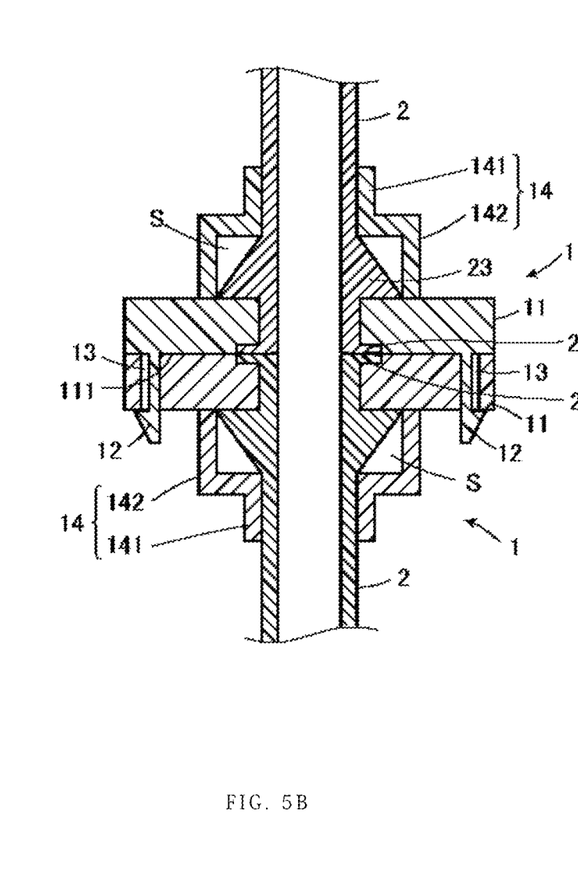
FIG. 5B is a cross-sectional view showing a connected state of the sterile connector of the embodiment.

This results in the connection state shown in FIG. 5B (cross-sectional schematic view showing the connected state of the connectors).

The end face 21 of the first (second) tube 2 is configured to project beyond the first (second) joining surface 111. When the first connector 1 and the second connector 1 are engaged, the end face 21 of the first tube and the end face 21 of the second tube are compressed with each other through the first protective sheet 3 and the second protective sheet 3. Thereafter, the first protective sheet 3 and the second protective sheet 3 are removed simultaneously, resulting in sterile and liquid-tight joining of the first tube 2 and the second tube 2. The first (second) tube 2 is a resilient, elastic, and flexible member such as a silicone tube, and the first (second) flange portion 22 being compressed thereto results in the connected state as shown in FIG. 5B.

In this embodiment, the end face 21 of the first tube and the end face 21 of the second tube have a projecting curve in the cross-section (cross-section along the longitudinal direction of the first tube 2) (FIG. 3), which causes the end face 21 of the first tube and the end face 21 of the second tube to line-contact, enhancing sealing property therebetween. This can improve their sterility and liquid-tightness. However, the present invention is not limited thereto, and it is preferable to make the cross-sectional shape of the end face 21 of the first tube and the end face 21 of the second tube to have more sealing property depending on the amount of projection of the end face 21 of the first tube and end face 21 of the second tube, the hardness and material of the tubes, etc.

As described above, the sterile connector of this embodiment is a connector that directly compresses the end faces of the tubes with each other, thereby reducing the number of intervening components between the tubes to be connected. Therefore, factors that may cause defects in sealing property (sterility) can be reduced as much as possible. The reduction in the number of components also reduces cost and simplifies assembly work. Moreover, since liquid does not contact the first connector 1 and the second connector 1 (liquid does not contact other than the tubes), a wider range of selection of materials used for the connector portion can be achieved. For example, by configuring the first connector from polypropylene, it is possible to fix the first protective sheet 3 made of polyethylene by thermal welding (ultrasonic thermal welding). This eliminates the need to use an adhesive to fix the two members so that they are prevented from peeling off even in an environment of −80° C., making it possible for use in a container for freezing and storing bulk drugs. Unlike the above, however, the first connector can be configured from polycarbonate, and in this case, it is possible to fix the first protective sheet 3 using an adhesive. According to the above, by using a proper adhesive, it is possible to fix the two members more firmly. Alternatively, the first connector can be configured from polycarbonate and polypropylene in a two-color molding. In other words, the area where the sterile connectors are fitted with each other (the area where the engaging projection 12 and engaging hole 13 are configured) can be configured from polycarbonate to increase strength, and the area where the protective sheet 3 is fixed (fixing region 3-2) can be configured from polypropylene so that the protective sheet 3 can be fixed by thermal welding (without using an adhesive).

In addition, as understood from FIGS. 4A-4B, according to the sterile connector of this embodiment, it is configured such that the inner diameter of the first (second) tube 2 does not substantially change, thus reducing the loss (pressure drop) at the connector portion during liquid transfer as much as possible. In particular, as shown in FIG. 5B, the inner diameters of the first tube and the second tube can be maintained equivalent even when the first and second connectors are engaged, thus minimizing the phenomenon of liquid remaining between the tubes.

According to the sterile connector of this embodiment, the first tube 2 has the first flange portion 22 and the first thick diameter portion 23, which are configured to sandwich the first body portion 11 therebetween, so that in the joint state shown in FIG. 5B, when an external force is applied (such as being pulled) to the first (second) tube 2, deformation of the end face 21 of the first tube 2 can be prevented, and contributes to maintaining sterility.

Furthermore, since the tip end portion 141 of the fitting portion 14 is configured to tighten the first tube 2, when the first tube 2 is pulled, the force is prevented from reaching the end face 21, which further contributes to maintaining sterility between the tubes.

In this embodiment, the first (second) spacing S "does not tighten the first (second) tube 2". The first tube 2 is a resilient, elastic, and flexible tube, such as a fluorine resin tube or silicone tube, and the first thick diameter portion 23 of the tube which is resilient, elastic, and flexible deforms within the first spacing S when an external force is applied to the tube (when pulled), etc. Since the first spacing S "does not tighten the first tube 2", the deformation is not inhibited and the first thick diameter portion 23 flexes in the spacing S. The flexure of the first thick diameter portion 23 is expected to further reduce the occurrence of defects such as an external force applied to the first tube 2 reaching the end face 21 of the first tube 2 causing deformation. However, in accordance with the material of the first tube 2, it is also possible to configure the fitting portion 14 without the spacing S (so that the large diameter portion 142 contacts the thick diameter portion 23, or so that the large diameter portion 142 tightens the thick diameter portion 23).

In the embodiment, an example is given where the first (second) second body portion is configured from polypropylene, to which the first (second) protective sheet of polyethylene is thermally welded. However, the present invention is not limited thereto.

For example, the first (second) body portion and the first (second) protective sheet may be configured from polycarbonate and polyethylene, respectively, and the first (second) protective sheet may be fixed to the first (second) body portion via an adhesive.

In the embodiment, an example is given where the second tube and the second connector have the same configurations as the first tube 2 and the first connector 1. However, the present invention is not limited thereto, and within the scope of including the concept of the present invention understood from the explanation given above, the second tube and the second connector can have different configurations from the first tube 2 and the first connector 1. For example, the engaging portion for engaging the first connector 1 and the second connector may be asymmetrical in shape so that the first connector 1 and the second connector are not identical members.

In the embodiment, an example is given where both the end face 21 of the first tube and the end face 21 of the second tube project beyond the first (second) joining surface 111. However, the present invention is not limited thereto. For example, one of the end face of the first tube and the end face 21 of the second tube may project from the first (second) joining surface and the other may be flush with the first (second) joining surface (the end face of the first tube and the end face of the second tube only need to be configured to be compressed when the first connector and the second connector are engaged).

In the embodiment, an example is given where both the end face 21 of the first tube and the end face 21 of the second tube have a projecting curve in their cross-section. However, the present invention is not limited thereto. For example, one of the end face of the first tube and the end face of the second tube can have a projecting curve in the cross-section, and the other can be a plane. With "a configuration where the end face of the first tube and the end face 21 of the second tube contact in line contact upon beginning of the contact", the contact pressure at the contact location can be increased and the degree of sealing can be improved compared to surface contact of the faces. When sufficient sealing can be obtained even in surface contact by the compression between the end faces of the first (second) tube by the aforementioned "structure in which the end face of the first (second) tube projects beyond the first (second) joining surface", the end face of the first tube and the end face of the second tube may be configured to be in surface contact at the beginning of their contact.

DESCRIPTION OF REFERENCE NUMERALS

1 . . . first (second) connector
11 . . . first (second) body portion
111 . . . first (second) joining surface
12 . . . first engaging member
13 . . . engaging hole
14 . . . first (second) fitting portion
141 . . . tip end portion
2 . . . first (second) tube
21 . . . end face
22 . . . flange portion
23 . . . first (second) thick diameter portion
3 . . . first (second) protective sheet
S . . . first (second) spacing

The invention claimed is:

1. A sterile connector comprising a first connector attached to a first tube, and a second connector attached to a second tube,
wherein the first connector includes:
a first body portion including a first joining surface;
a first engaging member for engaging with the second connector;
a first fitting portion that fits with the first tube, which is provided on a back surface of the first joining surface of the first body portion and which has a tip end portion for tightening the first tube; and
a first protective sheet which covers the first joining surface and an end face of the first tube and which is removed after the first connector is engaged with the second connector, and
wherein the second connector includes:
a second body portion including a second joining surface;
a second engaging member for engaging with the first connector; a second fitting portion that fits with the second tube, which is provided on a back surface of the second joining surface of the second body portion and which has a tip end portion for tightening the second tube; and
a second protective sheet which covers the second joining surface and an end face of the second tube and which is removed after the second connector is engaged with the first connector,
wherein the first connector and the second connector have the same shape,
wherein the first connector is attached to the first tube such that the end face of the first tube is positioned to project beyond the first joining surface, or the second connector is attached to the second tube such that the end face of the second tube is positioned to project beyond the second joining surface, and
wherein the sterile connector is configured such that, when the first connector and the second connector are engaged such that the first joining surface faces the second joining surface, the end face of the first tube and the end face of the second tube are compressed with each other.

2. The sterile connector according to claim 1,
wherein the first fitting portion comprises a first spacing where the first tube is not tightened, and
wherein the second fitting portion comprises a second spacing where the second tube is not tightened.

3. The sterile connector according to claim 2,
wherein the first tube comprises a first thick diameter portion where an outer diameter increases toward the first body portion in the first spacing, and
wherein the second tube comprises a second thick diameter portion where an outer diameter increases toward the second body portion in the second spacing.

4. The sterile connector according to claim 1,
wherein the end face of the first tube has a convex curve in cross-section along a longitudinal direction of the first tube, or
wherein the end face of the second tube has a convex curve in cross-section along a longitudinal direction of the second tube.

5. The sterile connector according to claim 1, wherein a tip end portion of the first tube and the tip end portion of the second tube are configured as a flange.

6. The sterile connector according to claim 1, configured such that inner diameters of the first tube and the second tube do not change.

7. The sterile connector according to claim 1,
wherein the first body portion and the second body portion are configured from polypropylene,
wherein the first protective sheet and the second protective sheet are configured from polyethylene, and
wherein the first protective sheet and the second protective sheet are fixed to the first body portion and the second body portion by thermal welding.

8. The sterile connector according to claim 1,
wherein the first body portion and the second body portion are configured from polycarbonate,
wherein the first protective sheet and the second protective sheet are configured from polyethylene, and
wherein the first protective sheet and the second protective sheet are fixed to the first body portion and the second body portion via an adhesive.

* * * * *